United States Patent
Falchi et al.

(12)

(10) Patent No.: US 8,168,787 B2
(45) Date of Patent: May 1, 2012

(54) PROCESS FOR THE PREPARATION OF IMATINIB AND INTERMEDIATES THEREOF

(75) Inventors: Alessandro Falchi, Sassari (IT); Ennio Grendele, Vicenza (IT); Riccardo Motterle, Vicenza (IT); Mariano Stivanello, Vicenza (IT)

(73) Assignee: F.I.S. Fabbrica Italiana Sintetici S.p.A., Alte di Montecchio Maggiore, Vicenza (IT)

( * ) Notice: Subject to any disclaimer, the term of this patent is extended or adjusted under 35 U.S.C. 154(b) by 410 days.

(21) Appl. No.: 12/515,105

(22) PCT Filed: Nov. 15, 2007

(86) PCT No.: PCT/IT2007/000804
§ 371 (c)(1),
(2), (4) Date: May 15, 2009

(87) PCT Pub. No.: WO2008/059551
PCT Pub. Date: May 22, 2008

(65) Prior Publication Data
US 2010/0076189 A1    Mar. 25, 2010

(30) Foreign Application Priority Data

Nov. 16, 2006 (IT) .......................... MI2006A002208
May 9, 2007 (IT) .......................... MI2007A000942

(51) Int. Cl.
*C07D 401/04* (2006.01)
(52) U.S. Cl. ...................................................... 544/331
(58) Field of Classification Search .................... 544/331
See application file for complete search history.

(56) References Cited

FOREIGN PATENT DOCUMENTS

| EP | 0 564 409 A1 | 10/1993 |
|---|---|---|
| WO | WO 2004/108699 A1 | 12/2004 |
| WO | WO 2006/071130 A2 | 7/2006 |

*Primary Examiner* — Deepak Rao
(74) *Attorney, Agent, or Firm* — Dickstein Shapiro LLP

(57) ABSTRACT

A process for the preparation of 4-methyl-N3-[4-(3-pyridinyl)-2-pyrimidinyl]-1,3-benzenediamine and analogues thereof, intermediates useful for the synthesis of Imatinib, or 4-[(4-methyl-1-piperazinyl)methyl]-N-[4-methyl-3-[[4-(3-pyridinyl)-2-pyrimidinyl]amino]phenyl]benzamide.

11 Claims, No Drawings

PROCESS FOR THE PREPARATION OF IMATINIB AND INTERMEDIATES THEREOF

This application is a 371 of PCT/IT2007/000804 filed Nov. 15, 2007.

TECHNICAL FIELD OF THE INVENTION

It is the object of the present invention a process for the preparation of 4-methyl-N-3-[4-(3-pyridinyl)-2-pyrimidinyl]-1,3-benzenediamine and analogues thereof, intermediates useful for the synthesis of Imatinib, or 4-[(4-methyl-1-piperazinyl)methyl]-N-[4-methyl-3-[[4-(3-pyridinyl)-2-pyrimidinyl]amino]phenyl]benzamide.

STATE OF THE ART

Imatinib mesylate, a molecule of Formula 9, is an important drug employed in the treatment of the chronic myeloid leukaemia.

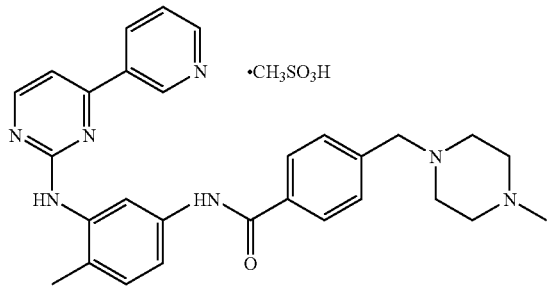

Its preparation has been first described in EP 564409 by Novartis, and it is summarized in the following Scheme 1. This document does not report the yields of the various preparative operations.

Scheme 1

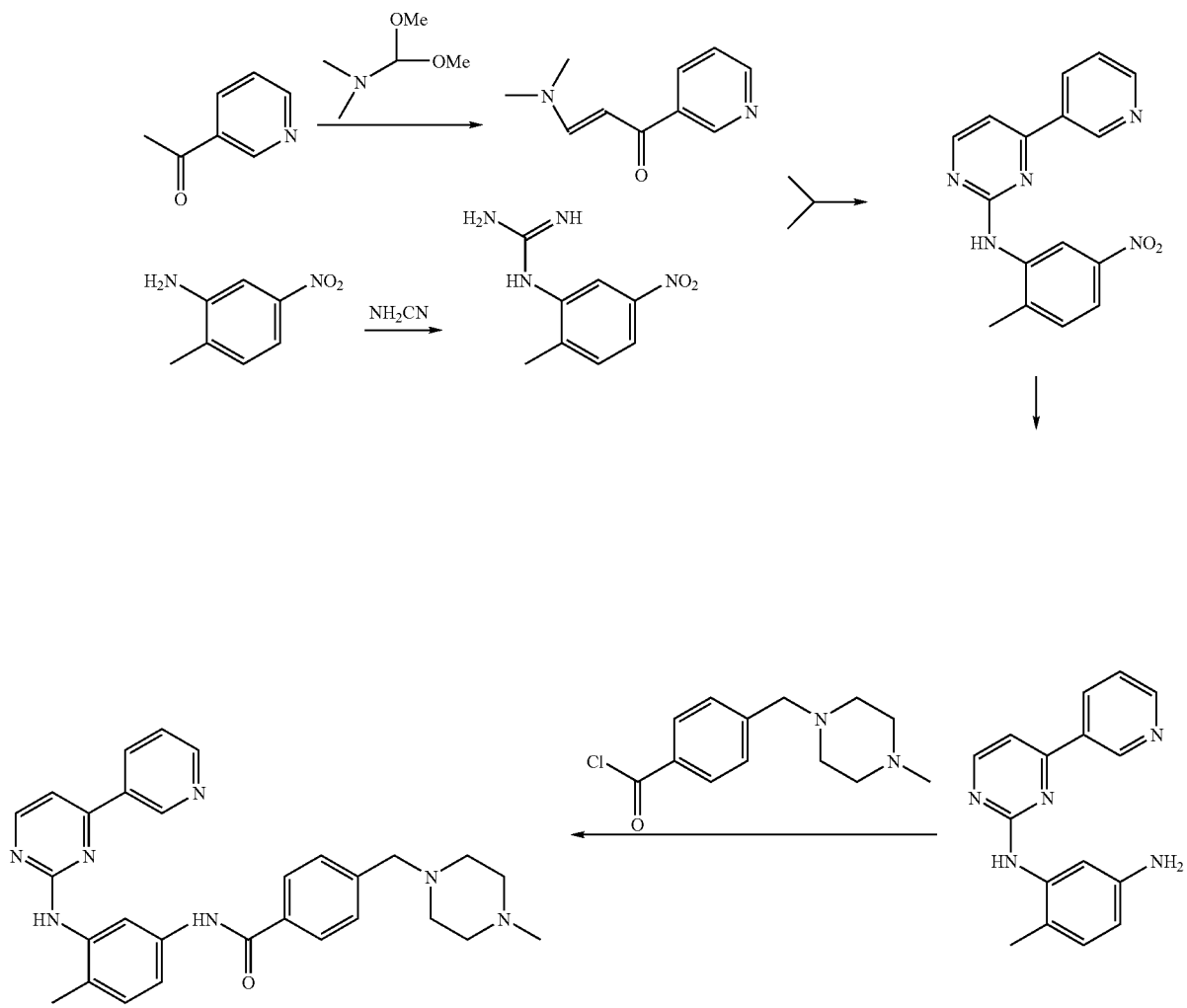

However, WO 2006/071130 reports that, by this synthetic way, the total yield of Imatinib does not exceed 15%. Furthermore, many steps have long and difficult work-ups and, for this reason, they are not suitable to an industrial application. Furthermore, N,N-dimethylformamide dimethyl acetal is an expensive reagent, and this makes this synthetic way not very economically advantageous. The above-listed problems are particularly relevant for the synthesis of the intermediate 4-methyl-N3-[4-(3-pyridinyl)-2-pyrimidinyl]-1,3-benzenediamine of Formula 8.

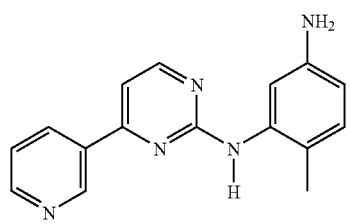

The technical problem to be solved in view of the prior art is therefore to provide a process for the preparation of 4-methyl-N3-[4-(3-pyridinyl)-2-pyrimidinyl]-1,3-benzenediamine and analogues thereof which proceeds with high yields, is easily able of being produced on industrial scale, and economically advantageous.

BRIEF DESCRIPTION OF THE INVENTION

The present invention relates to the preparation of 4-methyl-N3-[4-(3-pyridinyl)-2-pyrimidinyl]-1,3-benzenediamine and analogues thereof starting from β-oxo-3-pyridinpropanal, a salt thereof, or a enolether thereof, or from the β-oxo-3-pyridinepropionic acid o an ester thereof.

DETAILED DESCRIPTION OF THE INVENTION

It has been surprisingly found a process for the preparation of compounds of Formula 1

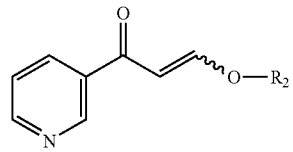

in which $R_1$ represents amino, nitro, halogen, hydroxy, $NH(CO)R_3$, $NHR_4$, $R_3$ represents 4-(halo-methyl)phenyl, 4-(hydroxymethyl)phenyl, 4-((4-methylpiperazinyl)carbonyl)phenyl, 4-(alkoxycarbonyl)phenyl, or 4-[(4-methyl-1-piperazinyl)methyl]phenyl, in which alkoxy means $C_1$-$C_4$ alkoxy, $R_4$ represents a protecting group for the amine group, comprising the steps of a) reacting the β-oxo-3-pyridinepropanal, a salt thereof, or a enolether thereof of Formula 17

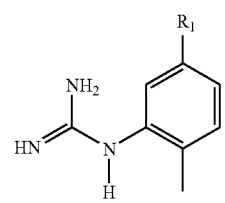

in which $R_2$ represents hydrogen, $C_1$-$C_4$ alkyl, benzyl, or phenyl, with an aryl guanidine of Formula 3

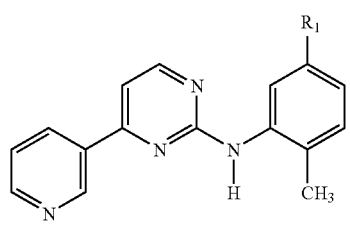

in which $R_1$ has the meaning described above, to yield the compound of Formula 19

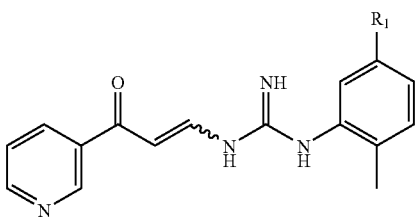

in which $R_1$ has the foregoing meaning, and b) cycling the intermediate of Formula 19 in the presence of a base.

$R_1$ preferably represents amino, nitro, $NH(CO)R_3$, $NHR_4$, more preferably amino or nitro;

$R_2$ preferably represents hydrogen, isopropyl, or n-butyl;

$R_3$ preferably represents 4-(chloromethyl)phenyl, or 4-[(4-methyl-1-piperazinyl)methyl]phenyl;

$R_4$ preferably represents a carboxamide, a solfonamide, or a carbamate, more preferably it represents a $COCH_3$, (CO)OBn, (CO)O-t-Bu, $(SO_2)Ph$, $(SO_2)(4$-Me-Ph) group;

When $R_1$ is a $NH(CO)R_3$ group, in which $R_3$ represents 4-(halo-methyl)phenyl, 4-(hydroxymethyl)phenyl, 4-((4-methylpiperazinyl)carbonyl)phenyl, 4-(alkoxycarbonyl)phenyl, in which alkoxy means $C_1$-$C_4$ alkoxy, the above-described synthesis will yield a more advanced intermediate in the synthesis of Imatinib than the 4-methyl-N3-[4-(3-pyridinyl)-2-pyrimidinyl]-1,3-benzenediamine compound of Formula 8; such intermediate will be able to be converted in Imatinib according to the modes known in the literature (see WO 2004108699, EP 52853, WO 2005005414, or Arch. Pharmacal Res., 27(11), 1093-1098 (2004)).

When $R_1$ is a $NH(CO)R_3$ group, in which $R_3$ represents 4-[(4-methyl-1-piperazinyl)methyl]phenyl, the above-described synthesis will directly yield Imatinib.

The reaction of cyclization b) requires the use of a base, preferably selected from the group consisting of sodium hydroxide, sodium carbonate, sodium $C_1$-$C_4$ alcoholates, potassium hydroxide, potassium carbonate, potassium $C_1$-$C_4$ alcoholates, lithium hydroxide, lithium carbonate, lithium $C_1$-$C_4$ alcoholates, caesium hydroxide, caesium carbonate, ammonia, and 4-dimethylaminopyridine, more preferably it is potassium hydroxide. The base can be absent in the step a), or it can be present even in the step a).

The above-described process comprises the optional step of isolation of the intermediate of Formula 19, provided that the step a) is not performed in the presence of the base employed in the step b); in this case, the intermediate 19 is achieved with high yield and purity. The synthesis is preferably carried out in a solvent selected from the group consisting of methanol, ethanol, isopropanol, n-butanol, dimethyl sulfoxide, dimethyl formamide, dimethyl acetamide, N-methylpyrrolidone, toluene, and mixtures thereof, more preferably isopropanol. The step a) is preferably carried out at a temperature ranging between 0° C. and 50° C. and in a time period between 2 and 6 hours, and the step b) preferably at a temperature ranging between 80° C. and 140° C. and in a time period between 6 and 24 hours.

A particularly preferred embodiment of the invention is a process for the preparation of 4-methyl-N3-[4-(3-pyridinyl)-2-pyrimidinyl]-1,3-benzenediamine of Formula 8

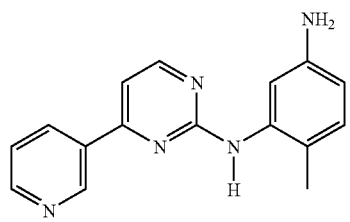

8 comprising the steps of
a) reacting the sodium salt of the β-oxo-3-pyridinepropanal of Formula 20 (or a tautomer thereof)

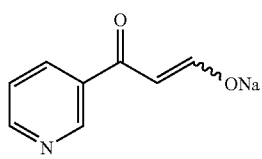

20 with the (2-methyl-5-aminophenyl)guanidine of Formula 21

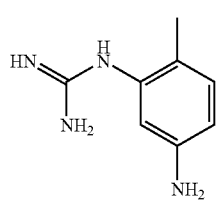

21 to yield the compound of Formula 22

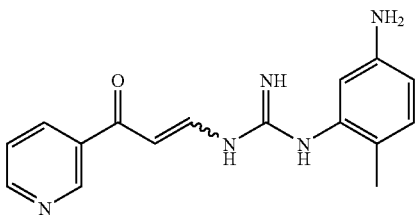

22 and b) cycling the intermediate of formula 22 in the presence of a base.

In fact, the (2-methyl-5-aminophenyl)guanidine reacts with the β-oxo-3-pyridinepropanal quicker than the (2-methyl-5-nitrophenyl)guanidine.

Following the addition of acid to the mixture of sodium salt of the β-oxo-3-pyridinepropanal of Formula 20 and (2-methyl-5-aminophenyl)guanidine of Formula 21 at room temperature, the precipitation of the product of formula 22, which can be filtered off, is achieved.

The raw 4-methyl-N3-[4-(3-pyridinyl)-2-pyrimidinyl]-1,3-benzenediamine is suitably crystallized from toluene in a 80% yield and purity above 99% (HPLC). Such quality of product is employed in the synthesis of Imatinib described in EP 564409.

The β-oxo-3-pyridinepropanal, or a enolether thereof, of Formula 17 is suitably generated by the addition of an acid to the salt of the β-oxo-3-pyridinepropanal 18

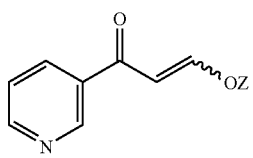

18 in which Z represents an alkaline or earth-alkaline metal, preferably sodium or potassium. When $R_2$ in the compounds of Formula 17 is different from hydrogen, the solvent employed for their preparation is the alcohol of Formula $R_2OH$. The acid is preferably hydrochloric acid or acetic acid.

The sodium salt of the β-oxo-3-pyridinepropanal of Formula 20 and the analogues thereof of Formula 18 can be prepared according to the teachings of DE 2125310, and can be isolated or employed 'in situ'.

The (2-methyl-5-aminophenyl)guanidine of Formula 21 and the analogues thereof of Formula 3 can be prepared according to the teachings of WO 2004110452.

Further object of the present invention is represented by the compounds of Formula 19

19 in which $R_1$ has the meaning described above.

Particularly preferred is the compound of Formula 22.

A further aspect of the present invention consists in a second process for the preparation of 4-methyl-N3-[4-(3- pyridinyl)-2-pyrimidinyl]-1,3-benzenediamine and analogues thereof starting from the β-oxo-3-pyridinepropionic acid or an ester thereof.

It has been surprisingly found a process for the preparation of compounds of Formula 1'

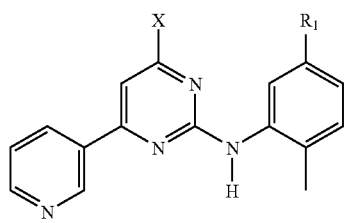

1' in which $R_1$ represents nitro, amino, halogen, hydroxy, NH(CO)$R_3$, NH$R_4$,

X represents hydrogen, chlorine, bromine, iodine, hydroxy, or O$R_5$, $R_3$ represents 4-(halo-methyl)phenyl, 4-(hydroxymethyl) phenyl, 4-((4-methylpiperazinyl)carbonyl)phenyl, 4-(alkoxycarbonyl)phenyl, or 4-[(4-methyl-1-piperazinyl) methyl]phenyl, in which alkoxy means $C_1$-$C_4$ alkoxy, $R_4$ represents a protecting group for the amine group, $R_5$ represents an activating group for the hydroxyl group, comprising the reaction of the β-oxo-3-pyridinepropionic acid or an ester thereof of Formula 2

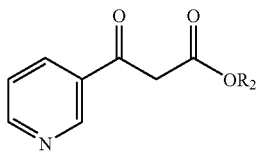

2 in which $R_2$ represents hydrogen, $C_1$-$C_4$alkyl, benzyl, or phenyl, with an aryl guanidine of Formula 3

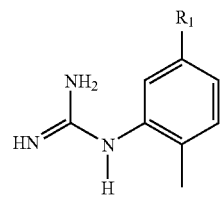

3 in which $R_1$ has the meaning described above.

$R_1$ preferably represents nitro, amino, NH(CO)$R_3$, NH$R_4$, more preferably nitro or amino;

X preferably represents hydrogen, chlorine, bromine, or hydroxy;

$R_2$ preferably represents methyl, ethyl, or isopropyl;

$R_3$ preferably represents 4-(chloromethyl)phenyl, or 4-[(4-methyl-1-piperazinyl)methyl]phenyl;

$R_4$ preferably represents a carboxamide, a sulphonamide, or a carbamate, more preferably it represents a COCH$_3$, (CO) OBn, (CO)O-t-Bu, (SO$_2$)Ph, (SO$_2$)(4-Me-Ph) group;

$R_5$ preferably represents a carboxylic or sulfonic ester, more preferably a —CO-alkyl($C_1$-$C_4$), or —SO$_2$R$_6$ group, in which $R_6$ is selected from methyl, trifluoromethyl, phenyl, 4-methylphenyl, 4-nitrophenyl, 4-bromophenyl.

A further aspect of the present invention relates to the compounds of Formula 1'

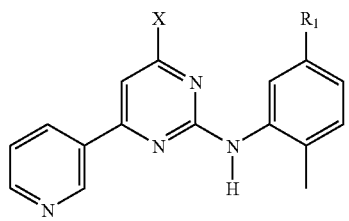

1' in which $R_1$ has the foregoing meaning, and X represents chlorine, bromine, iodine, hydroxy, or O$R_5$.

X preferably represents chlorine, bromine, or hydroxy.

When X represents a hydroxyl group, the compound of Formula 1' (indicated above in the enolic form) can be under a tautomeric ketonic form.

A particularly preferred embodiment of the invention is a process for the preparation of 6-hydroxy-N-(2-methyl-5-nitrophenyl)-4-(3-pyridyl)-2-pyrimidine amine of Formula 4

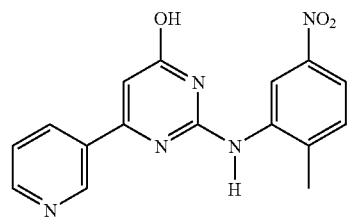

4 comprising the reaction of the ethyl β-oxo-3-pyridine propionate 5

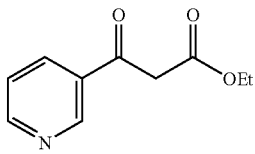

5 with (2-methyl-5-nitrophenyl) guanidine of Formula 6.

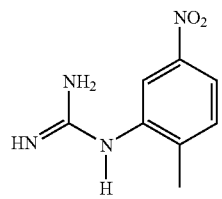

6

The reaction is preferably carried out in a solvent selected from the group consisting of dimethylformamide, N-methylpyrrolidone, isopropanol, 2-methoxyethyl ether, dimethyl sulfoxide, more preferably in N-methylpyrrolidone, at a temperature preferably ranging between 100° C. and 160° C. and in a time period preferably ranging between 6 and 18 hours.

The reaction is promoted by using high temperatures, which allow the progress of the condensation and the distilling off of the alcohol, water, and the by-products which form during the reaction.

The β-oxo-3-pyridinepropionic acid or an ester thereof of Formula 2 is preferably employed in a molar ratio ranging between 1.2:1 and 2:1 in relation to the aryl guanidine of Formula 3.

The ethyl β-oxo-3-pyridine propionate 5 and, by analogy, the compounds of Formula 2 can be prepared according to the teachings of *Arch. Pharm.*, 291, 12-22 (1958) and *J. Am. Chem. Soc.*, 63, 490-492 (1941).

By operating according to the present invention it is possible to achieve the 6-hydroxy-N-(2-methyl-5-nitrophenyl)-4-(3-pyridyl)-2-pyrimidine amine of Formula 4 in a yield above 70% and with a purity above 95%. Such product is employed in the synthesis of 6-chloro-N-(2-methyl-5-nitrophenyl)-4-(3-pyridyl)-2-pyrimidine amine described herein below.

The above-described process comprises the optional halogenation step in order to prepare the compounds of Formula 1', in which X represents chlorine, bromine, or iodine, and $R_1$ has the foregoing meaning, comprising the reaction of the compounds of Formula 1', in which X represents hydroxyl, or $OR_5$, and $R_5$ has the foregoing meaning, with a halogenating agent.

A particularly preferred embodiment of the invention is a process for the preparation of 6-chloro-N-(2-methyl-5-nitrophenyl)-4-(3-pyridyl)-2-pyrimidine amine of formula 7 reagent promotes the progress of the reaction, and it can be subsequently recovered by reduced-pressure distillation.

The compound of Formula 1', in which X represents chlorine, bromine, or iodine, can be purified by crystallization or crushing from one or more solvents preferably selected from the group consisting of water, toluene, xylene, ethyl acetate, isopropyl acetate and isopropanol, more preferably from water and toluene.

By operating according to the present invention, it is possible to achieve raw 6-chloro-N-(2-methyl-5-nitrophenyl)-4-(3-pyridyl)-2-pyrimidine amine hydrochloride in quantitative yield and with purity above 75%. Such quality of product is employed in the synthesis of N-(2-methyl-5-aminophenyl)-4-(3-pyridyl)-2-pyrimidine amine described herein below.

The above-described process comprises the optional reduction step in order to prepare the compounds of Formula 1', in which X represents hydrogen, and $R_1$ has the foregoing meaning, comprising the reaction of the compounds of Formula 1', in which X represents chlorine, bromine, or iodine, or $-OSO_2R_6$, where $R_6$ has the foregoing meaning, with a reducing agent.

When $R_1$ represents a nitro group, the reduction allows concomitantly performing the removal of the halogen from the pyrimidine ring and the reduction of the nitro group to amino of the benzenic ring. A particularly preferred embodiment of the invention is a process for the preparation of 4-methyl-N3-[4-(3-pyridinyl)-2-pyrimidinyl]-1,3-benzenediamine of Formula 8

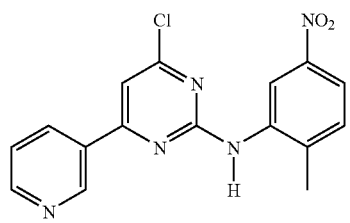

7

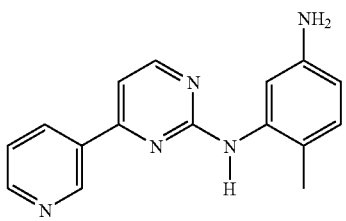

8 comprising the reaction of 6-hydroxy-N-(2-methyl-5-nitrophenyl)-4-(3-pyridyl)-2-pyrimidine amine with a halogenating agent.

The halogenating agent is preferably selected from the group consisting of phosphorous oxychloride, phosphorous trichloride, phosphorous pentachloride, thionyl chloride, phosphorous oxybromide, phosphorous tribromide, phosphorous pentabromide, and phosphorous triiodide, more preferably it is phosphorous oxychloride.

The reaction is promoted by the use of a base, preferably selected from the group consisting of sodium hydroxide, sodium carbonate, sodium bicarbonate, potassium hydroxide, potassium carbonate, potassium bicarbonate, caesium hydroxide, caesium carbonate, caesium bicarbonate, more preferably potassium carbonate, preferably added in amounts of 1-3 equivalents.

The reaction is preferably carried out in a solvent selected from toluene and xylene, or in the absence of a solvent, more preferably in the absence of a solvent. The reaction is preferably carried out at a temperature ranging between 20° C. and 100° C. and in a time period between 3 and 18 hours.

The reaction is promoted by the use of the halogenating agent in excess relative to the compound of Formula 1', preferably in a molar ratio between 8:1 and 20:1; such excess of comprising the reaction of the 6-chloro-N-(2-methyl-5-nitrophenyl)-4-(3-pyridyl)-2-pyrimidine amine of Formula 7 with a reducing agent.

The reducing agent is preferably selected from the group consisting of hydrogen, cyclohexadiene, ammonium formate, tin dichloride, tin, nickel chloride, nickel, lithium aluminium hydride, sodium aluminium hydride, sodium hydrosulfite, more preferably it is hydrogen. In the case of the employment of hydrogen, cyclohexadiene, and ammonium formate, the reaction is carried out in the presence of a catalyst, preferably based on palladium or nickel, more preferably selected from the group consisting of palladium on carbon, palladium on barium sulphate, and palladium on calcium carbonate. The catalyst is preferably employed in amounts between 0.02 and 0.1 in moles relative to the compound to be reduced. The reaction is preferably carried out in the presence of a base, preferably selected from the group consisting of triethylamine, pyridine, sodium hydroxide, sodium carbonate, sodium bicarbonate, potassium hydroxide, potassium carbonate, potassium bicarbonate, caesium hydroxide, caesium carbonate, caesium bicarbonate, more preferably it is triethylamine.

The reduction is preferably carried out in a solvent selected from the group consisting of ethanol, methanol, isopropanol, ethyl acetate, isopropyl acetate, tetrahydrofuran and dimethylformamide, more preferably in ethanol, it is preferably carried out at a temperature ranging between 20 and 80° C. and in a time period between 2 and 18 hours.

The compound of Formula 1' employed as a reagent, in which X represents chlorine, bromine, or iodine, can be used as the free base, or as a salt. The addition of the above-described base allows neutralizing the acid which forms during the reaction, and solubilize the reagent of Formula 1', if this is in the salt form.

The compound of Formula 1' achieved by the reduction, in which X represents hydrogen, is suitably purified by crystallization, preferably from toluene or methanol.

By operating according to the present invention, it is possible to achieve raw 4-methyl-N3-[4-(3-pyridinyl)-2-pyrimidinyl]-1,3-benzenediamine of Formula 8 in high yield and purity. The raw 4-methyl-N3-[4-(3-pyridinyl)-2-pyrimidinyl]-1,3-benzenediamine is suitably purified by ricrystallization from toluene or methanol in a 80% yield and purity above 99% (HPLC). Such quality of product is employed in the synthesis of Imatinib described in EP 564409.

Alternatively, the step reduction can be performed before the halogenation step. In this case the above-described process comprises the optional reduction step in order to prepare the compounds of Formula 1', in which $R_1$ represents an amino group and X represents hydroxy or $OR_5$, and $R_5$ has the foregoing meaning, comprising the reaction of the compounds of Formula 1', in which $R_1$ represents a nitro group, with a reducing agent. However, in order to prepare the compound 4-methyl-N3-[4-(3-pyridinyl)-2-pyrimidinyl]-1,3-benzenediamine of Formula 8, it will be necessary that a further reduction step follows the halogenation step in order to remove the X group.

When $R_1$ represents a $NHR_4$ group, in which $R_4$ represents a protecting group for the amine group, or X represents a $OR_5$ group, in which $R_5$ represents an activating group for the hydroxyl group, it will be necessary to provide for further introduction and removal steps of the protecting or activating groups in order to achieve the 4-methyl-N3-[4-(3-pyridinyl)-2-pyrimidinyl]-1,3-benzenediamine compound of Formula 8. In particular, the synthesis process for the compounds of Formula 1', in which X represents a —$OSO_2R_6$ group, and $R_6$ has the foregoing meaning, comprises the reaction of the compounds of Formula 1', in which X represents hydroxy, with a sulfonilating agent, preferably $R_6SO_2Y$, in which Y represents chlorine, bromine, iodine, —$OSO_2R_6$.

When $R_1$ is a $NH(CO)R_3$ group, in which $R_3$ represents 4-(halo-methyl)phenyl, 4-(hydroxymethyl)phenyl, 4-((4-methylpiperazinyl)carbonyl)phenyl, 4-(alkoxycarbonyl)phenyl, in which alkoxy means $C_1$-$C_4$ alkoxy, the above-described synthesis will yield a more advanced intermediate in the synthesis of Imatinib compared to the 4-methyl-N3-[4-(3-pyridinyl)-2-pyrimidinyl]-1,3-benzenediamine compound of Formula 8.

When $R_1$ is a $NH(CO)R_3$ group, in which $R_3$ represents 4-[(4-methyl-1-piperazinyl)methyl]phenyl, the above-described synthesis will directly yield Imatinib.

A further aspect of the present invention consists in a third process for the preparation of 4-methyl-N3-[4-(3-pyridinyl)-2-pyrimidinyl]-1,3-benzenediamine and analogues thereof starting from the β-oxo-3-pyridinepropionic acid or an ester thereof.

It has been surprisingly found a process for the preparation of compounds of Formula 1

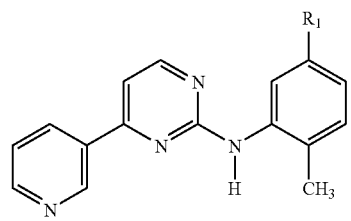

1 in which $R_1$ represents nitro, amino, halogen, hydroxy, $NH(CO)R_3$, $NHR_4$, $R_3$ represents 4-(halo-methyl)phenyl, 4-((4-methylpiperazinyl)carbonyl)phenyl, 4-(hydroxymethyl)phenyl, 4-(alkoxycarbonyl)phenyl, or 4-[(4-methyl-1-piperazinyl)methyl]phenyl, in which alkoxy means $C_1$-$C_4$ alkoxy.

$R_4$ represents a protecting group for the amine group, comprising the steps of:

a) reacting the β-oxo-3-pyridinepropionic acid or an ester thereof of Formula 2

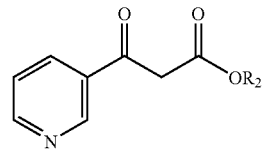

2 in which $R_2$ represents hydrogen, $C_1$-$C_4$ alkyl, benzyl, or phenyl, with an orthoformate of Formula $HC(OR_7)_3$, in which $R_7$ represents $C_1$-$C_4$ alkyl, benzyl, or phenyl, to yield the enolether of Formula 10

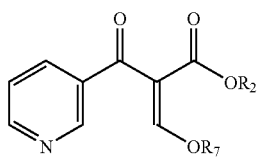

10 in which $R_2$ and $R_7$ have the above-described meaning, b) reacting the enolether of Formula 10 with an aryl guanidine of Formula 3

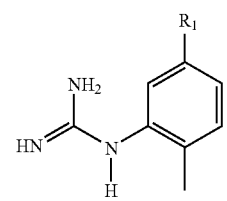

3 in which $R_1$ has the above-described meaning, to yield the compound of Formula 11

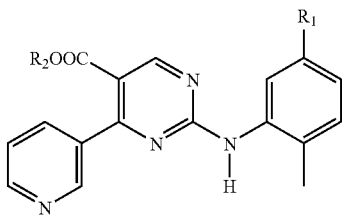

in which R₁ and R₂ have the above-described meaning, c) removing the COOR₂ group.

R₁ preferably represents nitro, amino, NH(CO)R₃, NHR₄, more preferably nitro or amino;

R₂ preferably represents methyl, ethyl, or isopropyl;

R₃ preferably represents 4-(chloromethyl)phenyl, or 4-[(4-methyl-1-piperazinyl)methyl]phenyl;

R₄ preferably represents a carboxamide, a sulphonamide, or a carbamate, more preferably it represents a COCH₃, (CO)OBn, (CO)O-t-Bu, (SO₂)Ph, (SO₂)(4-Me-Ph) group;

R₇ preferably represents methyl, ethyl, or phenyl.

A further aspect of the present invention relates to the compounds of Formula 10

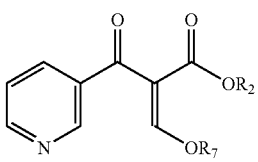

in which R₂ and R₇ have the meaning set forth above. A further aspect of the present invention relates to the compounds of formula 11

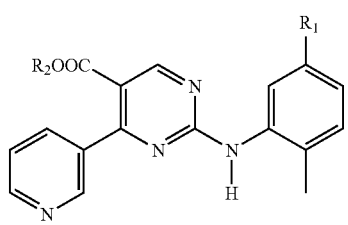

in which R₁ has the meaning described above, and R₂ represents hydrogen, C₁-C₄ alkyl, benzyl, or phenyl, or an alkaline or an earth-alkaline metal.

R₂ preferably represents hydrogen, methyl, ethyl, isopropyl, sodium, or potassium.

A particularly preferred embodiment of the invention is a process for the preparation of N-(2-methyl-5-nitrophenyl)-4-(3-pyridyl)-2-pyrimidine amine of Formula 13

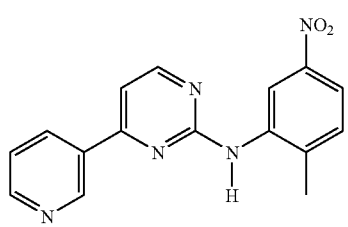

comprising the steps of:
a) reacting the ethyl β-oxo-3-pyridine propionate 5

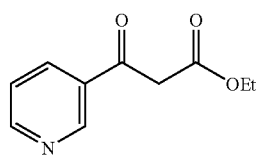

with triethyl orthoformate of Formula HC(OEt)₃ to yield the ethyl α-(etoxymethylene)-β-oxo-3-pyridine propionate of Formula 12

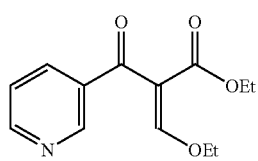

b) reacting the compound of Formula 12 with an aryl guanidine of Formula 6

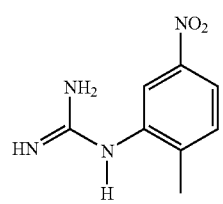

to yield the ethyl 2-[(2-methyl-5-nitrophenyl)amino]-4-(3-pyridinyl)pyrimidine-5-carboxylate of Formula 14

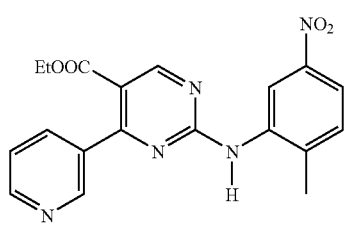

c) removing the COOEt group.

In the case where the compound of Formula 2 is the β-oxo-3-pyridine propionic acid (R₂=H), by reaction with the orthoformate of Formula HC(OR$_7$)$_3$ a compound of Formula 10 will be achieved in which R$_2$ is equal to R$_7$.

The step a) is preferably, but not necessarily, performed in the presence of an anhydride or an acid. The anhydride is preferably acetic anhydride, and the acid is preferably selected from the group consisting of pyridinium p-toluenesulfonate, dry hydrochloric acid, dry hydrobromic acid, sulforic acid, methanesulfonic acid, trifluoromethanesulfonic acid, benzenesulfonic acid, p-toluenesulfonic acid, more preferably it is pyridinium p-toluenesulfonate. The anhydride is preferably employed in an amount ranging between 1 and 3 equivalents, while the acid is preferably employed in amounts ranging between 0.001 and 0.1 equivalents relative to the compound of Formula 2.

The orthoformate is preferably employed as a solvent, with an excess between 1 and 6 volumes relative to the compound of Formula 2, and the excess can be recovered at the end of the reaction by distillation.

The reaction is preferably carried out at a temperature between 100° C. and 140° C. and in a time period between 1 and 5 hours, by distillating the R$_7$OH alcohol which develops during the condensation.

The ethyl α-(etoxymethylene)-β-oxo-3-pyridine propionate compound of Formula 12 is generally achieved in quantitative yield and with purity above 80%. Such quality of product is employed in the step b).

The step b) is preferably carried out in a high-boiling organic solvent, preferably selected from the group consisting of toluene, xylene, chlorobenzene, dimethyl sulfoxide, N-methylpyrrolidone, isopropyl acetate, still more preferably in toluene. The reaction is preferably carried out at a temperature ranging between 100° C. and 150° C. in a time period between 30 minutes and 5 hours, by distilling off the alcohol and water which form during the reaction.

The compound of Formula 10 is preferably employed in molar excess relative to the aryl guanidine of Formula 3.

The compound of Formula 11 can be isolated at the end of the reaction by cooling the reaction mixture and filtrating the crystallized product. The ethyl 2-[(2-methyl-5-nitrophenyl)amino]-4-pyridine-3-yl-pyrimidine-5-carboxylate 14 is achieved in yield above 85% and purity above 97% (HPLC).

The step c) preferably comprises the steps of c1) hydrolyzing the compounds of Formula 11 to yield the compounds of Formula 15

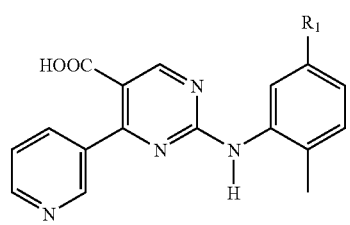

c2) removing the COOH group by decarboxylation.

A particularly preferred embodiment of the invention is a process for the preparation of N-(2-methyl-5-nitrophenyl)-4-(3-pyridyl)-2-pyrimidine amine of Formula 13 comprising the steps of:

c1) hydrolyzing the ethyl 2-[(2-methyl-5-nitrophenyl)amino]-4-(3-pyridinyl)pyrimidine-5-carboxylate of Formula 14 to yield the 2-[(2-methyl-5-nitrophenyl)amino]-4-(3-pyridinyl)pyrimidine-5-carboxylic acid of Formula 16

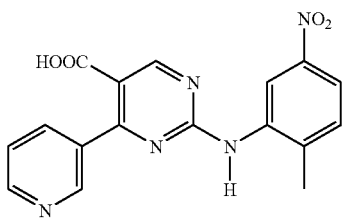

c2) removing the COOH group by decarboxylation.

The hydrolysis step c1) can be performed both in the presence of an acid, and in the presence of a base.

The acid is preferably a mineral acid, preferably selected from the group consisting of sulforic, hydrochloric, bromhydric, and percloric acid, preferably it is hydrochloric acid.

The base is preferably an inorganic base, preferably selected from sodium carbonate, sodium hydroxide, potassium carbonate, potassium hydroxide, lithium carbonate, lithium hydroxide, more preferably sodium carbonate, and it is preferably employed in a molar ratio between 1:1 and 3:1 relative to the ester of Formula 11.

The step c1) is preferably carried out in water or an alcohol, or mixtures thereof. The alcohol is preferably selected from the group consisting of methanol, ethanol, isopropanol, more preferably it is ethanol.

The reaction is preferably carried out at a temperature between 80 and 100° C., in a time period between 1 and 18 hours, and in distillation conditions suitable to complete the conversion.

The compounds of Formula 15 can be isolated by cooling the reaction mixture and, in the case of using a base in order to perform the hydrolysis, by acidifying the reaction mixture with an acid, achieving the product precipitation as a crystalline solid which can be regenerated by filtration. Alternatively, above all in the case of a basic hydrolysis, it is possible to isolate the compounds of Formula 15 as the relative salts.

The 2-[(2-methyl-5-nitrophenyl)amino]-4-(3-pyridinyl)pyrimidine-5-carboxylic acid of Formula 16 is achieved in a yield above 95% and purity above 95%.

The decarboxylation step c2) is preferably carried out at high temperature and in the presence of an acid, as for the step c1), or in the presence of a cupper-based catalyst, preferably selected from the group consisting of metallic cupper and cupper(II) oxide, more preferably cupper(II) oxide. The catalyst is preferably employed in amounts between 0.01 and 0.1 moles relative to the reagent of Formula 15. The employment of the cupper allows for a better progress of the reaction, minimizing degradation side-reaction.

The decarboxylation is preferably carried out in a solvent selected from the group consisting of quinoline, N-methylpyrrolidone, and sulfolane, still more preferably in N-methylpyrrolidone. The reaction is preferably carried out at a temperature between 160 and 200° C. and in a time period between 0.5 and 4 hours.

The steps c1) and c2) can be carried out in the same reaction conditions by processing the compounds of Formula 11 with an acid, preferably with hydrochloric acid.

The N-(2-methyl-5-nitrophenyl)-4-(3-pyridyl)-2-pyrimidine amine of Formula 13 is achieved, following basification and filtration, in quantitative yield and purity above 95%. Such quality of product is employed in the synthesis of the Imatinib and the analogues thereof described in EP 564409.

From the compounds of Formula 1, in which R$_1$ represents a nitro group, it is possible to achieve the compounds of Formula 1, in which $R_1$ represents an amino group, and in particular the 4-methyl-N3-[4-(3-pyridinyl)-2-pyrimidinyl]-1,3-benzenediamine of Formula 8 according to the above-described reduction process.

Finally, the present invention provides a simple method for the production of 4-methyl-N3-[4-(3-pyridinyl)-2-pyrimidinyl]-1,3-benzenediamine and the analogues thereof, having the following advantages:

1) unlike EP 564409, it does not use N,N-dimethylformamide dimethylacetale, an expensive starting material;
2) the procedures described are easy and can be readily transferred to a productive plant;
3) the recovery and recycling of many of the reagents used in excess are possible, thus allowing incrementing the yield without affecting the production costs;
4) the synthesis of 4-methyl-N3-[4-(3-pyridinyl)-2-pyrimidinyl]-1,3-benzenediamine of Formula 8 starting from the salt of the β-oxo-3-pyridinepropanal 21 has a whole yield equal to or above 80%, the synthesis of N-(2-methyl-5-nitrophenyl)-4-(3-pyridyl)-2-pyrimidine amine of Formula 13 starting from ethyl α-(etoxymethylene)-β-oxo-3-pyridine propionate 12 has a whole yield equal to or above 70%, and the synthesis of 4-methyl-N3-[4-(3-pyridinyl)-2-pyrimidinyl]-1,3-benzenediamine of Formula 8 starting from ethyl β-oxo-3-pyridine propionate 5 has a whole yield equal to or above 60%, thus making these processes among the most economically advantageous between those described in the literature.

Further features and advantages of the process of the invention will be clear from the description set forth below of preferred exemplary embodiments, which are given by way of non-limiting example.

EXAMPLES

Example 1

4-methyl-N3-[4-(3-pyridinyl)-2-pyrimidinyl]-1,3-benzenediamine 8

Under inert atmosphere, 16 g sodium salt of β-oxo-3-pyridinepropanal, with HPLC purity of 99% (A %) and 25% salt content (residue by calcination), and 11.7 g (2-methyl-5-aminophenyl)guanidine in 115 mL n-butanol is suspended. 9 mL acetic acid is added, and the mixture is stirred at room temperature for an hour. 6 g potassium hydroxide is added portionwise, and the mixture is refluxed for 18 hours, removing the water with a Dean Stark apparatus. Once completed the conversion, the suspension is cooled and the organic layer is washed with water. The organic layer is concentrated to a small volume, and toluene is added. The precipitate is filtrated, yielding, upon drying, 15.5 g of product with HPLC purity of 99.2% (A %), identified through LC-MS and $^1$H-NMR.

LC-MS: $[M+1]^+=278$.

$^1$H-NMR (300 MHz, DMSO-$d_6$): δ (ppm) 2.02 (s, 3H); 4.85 (s, 2H); 6.31 (d, 1H); 6.76 (s, 1H); 6.84 (d, 1H); 7.33 (d, 1H); 7.50 (m, 1H); 8.38 (d, 1H); 8.43 (d, 1H); 8.66 (bs, 1H); 9.22 (s, 1H).

Example 2

1-(5-amino-2-methylphenyl)-3-[(3-oxo-3-(3-pyridinyl)-1-prop-1-enyl]guanidine 22

Under inert atmosphere, 10 g sodium salt of β-oxo-3-pyridinepropanal, with HPLC purity of 99% (A %) and salt content of 25% (residue by calcination), in 80 mL isopropanol is suspended. 24 mL of a 15% solution of hydrochloric acid in isopropanol is added, and the mixture is stirred at room temperature for an hour. 7 g (2-methyl-5-aminophenyl) guanidine is added portionwise, and the mixture is stirred at room temperature for 12 hours. Once completed the conversion, the precipitate is filtrated, yielding, upon drying, 13.5 g of product with HPLC purity of 98% (A %) and salt content of 30% (residue by calcination), identified through LC-MS.

LC-MS: $[M+1]^+=296$.

Example 3

N-(2-methyl-5-nitrophenyl)-4-(3-pyridinyl)-2-pyrimidine amine 1 ($R_1=NO_2$)

Under inert atmosphere, 5 g of sodium salt of the β-oxo-3-pyridinepropanal, with HPLC purity of 99% (A %) and salt content of 25% (residue by calcination), and 8 mL hydrochloric acid in isopropanol in 50 mL toluene is suspended. 3.7 g (2-methyl-5-nitrophenyl)guanidine is added, and the mixture is stirred at room temperature for an hour. The mixture is refluxed for 18 hours, removing the water with a Dean Stark apparatus. Once completed the conversion, the suspension is cooled to 10° C., and the precipitate is filtrated; this is crushed in warm water, yielding, upon filtration and drying, 2.5 g of product with HPLC purity of 96% (A %), identified through GC-MS.

MS m/e (int. rel.): 307 (M+) (100); 292 (76); 260 (63); 246 (38).

Example 4

Ethyl α-(etoxymethylene)-β-oxo-3-pyridine propionate 12

Under inert atmosphere 20 g ethyl β-oxo-3-pyridine propionate in 100 mL triethyl orthoformate are dissolved. 0.2 g pyridinium p-toluenesulfonate is added, and the mixture is refluxed for three hours, distilling about 13 mL of by-products. Once completed the conversion, the mixture is cooled at room temperature and the triethyl orthoformate is distilled off at a reduced pressure. The residue is taken again with 80 mL toluene, and the mixture is processed with decolorizing charcoal. The solution is reduced-pressure concentrated to a residue, yielding 26 g of product as a dark oil with 80% HPLC titre (A %). The product is identified through GC-MS.

MS m/e (int. rel.): 249 (M+) (8); 204 (28); 192 (22); 174 (30); 159 (100); 115 (38); 106 (100).

Example 5

Ethyl 2-[(2-methyl-5-nitrophenyl)amino]-4-(3-pyridinyl)pyrimidine-5-carboxylate 14

Under inert atmosphere 19 g ethyl α-(etoxymethylene)-β-oxo-3-pyridine propionate and 14.8 g (2-methyl-5-nitrophenyl)guanidine (achieved from the respective nitrate salt by treatment with aqueous soda in THF) in 200 mL toluene is dissolved, and the solution is refluxed distilling off about 25 mL tops. Once completed the conversion, the hot solution is processed with decolorizing charcoal, cooled to 0° C., and the precipitate is filtrated. Upon drying, 25.5 g of product with HPLC purity of 97% (A %) is achieved, identified through GC-MS and $^1$H-NMR.

MS m/e (int. rel.): 379 (M+) (100); 364 (37); 350 (60); 332 (23); 304 (18).

¹H NMR (300 MHz, CDCl₃): δ (ppm)=1.20 (t, J=7.1, 3H); 2.47 (s, 3H); 4.25 (q, J=7.1, 2H); 7.37 (sa, 1H); 7.40 (s, 1H); 7.46 (m, 1H); 7.90 (dd, J=8.4, J=2.4, 2H); 8.05 (m, 1H); 8.71 (dd, J=4.8, J=1.6, 1H); 9.01 (s, 1H); 9.27 (d, J=2.2, 1H).
M.p.=125-130° C.

Example 6

2-[(2-methyl-5-nitrophenyl)amino]-4-(3-pyridinyl) pyrimidine-5-carboxylic acid 16

23 g ethyl 2-[(2-methyl-5-nitrophenyl)amino]-4-(3-pyridinyl)pyrimidine-5-carboxylate and 19 g sodium carbonate in a mixture composed by 150 mL water and 150 mL ethanol is suspended. It is refluxed for three hours distilling the ethanol, and compensating with water the volume loss. Once completed the conversion, it is cooled to 50° C. and adjusted to pH 6 with acetic acid. The suspension is filtrated, yielding, upon drying, 20 g of product with HPLC purity of 95% (A %), which is identified through ¹H-NMR.

¹H NMR (300 MHz, DMSO-d₆): δ (ppm)=2.42 (s, 3H); 3.3 (sa, 2H) 7.49 (m, 1H); 7.55 (m, 1H); 7.98 (m, 2H); 8.57 (m, 1H); 8.65 (dd, J=4.6, J=1.5, 1H); 8.73 (d, J=1.7, 1H) 8.96 (s, 1H).
M.p.=299.5-302.0° C. with gas development.

Example 7

N-(2-methyl-5-nitrophenyl)-4-(3-pyridinyl)-2-pyrimidine amine 13

To 25 mL N-methylpyrrolidone, 5.0 g 2-[(2-methyl-5-nitrophenyl)amino]-4-(3-pyridinyl)pyrimidine-5-carboxylic acid and 0.2 g cupric oxide is added. The mixture is heated to 180° C. for 2 hours, then cooled to 60° C., and 30% aqueous ammonia 1 mL and 50 mL water is added. It is cooled to 25° C., and the precipitate is filtrated, yielding, upon drying, 4.3 g of product with HPLC purity of 97% (A %), which is identified through GC-MS.

MS m/e (int. rel.): 307 (M+) (100); 292 (76); 260 (63); 246 (38).

Example 8

N-(2-methyl-5-nitrophenyl)-4-(3-pyridinyl)-2 pyrimidine amine 13

140 g ethyl 2-[(2-methyl-5-nitrophenyl)amino]-4-(3-pyridinyl)pyrimidine-5-carboxylate and 109 g potassium carbonate is suspended in a mixture composed by 1050 mL water and 560 mL ethanol. The mixture is refluxed for 1 hour, then 700 mL solvent are slowly distilled. Once completed the conversion, the mixture is cooled to 80° C. and it is adjusted to pH a 7 with 95 mL acetic acid. 560 mL N-methylpyrrolidone and 0.9 g CuO is added. The water present is distilled under reduced pressure, and the mixture is heated to 175-180° C. for 2 hours. Once completed the conversion, the mixture is cooled to 80-90° C., 1000 mL water and 5 g EDTA is slowly added, the mixture is stirred at room temperature, the product is filtrated and washed with water. Upon drying, 108 g of product with HPLC purity of 95% (A %) is achieved. This can be recrystallized from 10 volumes of 95:5 xylene/N-methylpyrrolidone to yield a product with 98% purity (A %) in a 80% yield.

Example 9

Sodium 2-[(2-methyl-5-nitrophenyl)amino]-4-(3-pyridinyl)pyrimidine-5-carboxylate 1.0 g ethyl 2-[(2-methyl-5-nitrophenyl)amino]-4-(3-pyridinyl)pyrimidine-5-carboxylate and 0.8 g sodium carbonate in 20 mL ethanol and 4 mL water is suspended. The mixture is refluxed for 4 hours by distillating the ethanol and compensating with water the volume loss. The mixture is cooled at room temperature, and the precipitate is filtrated, yielding 0.84 g of product.
M.p.=363° C. with decomposition.

Example 10

Ethyl α-(etoxymethylene)-β-oxo-3-pyridine propionate 12

Under inert atmosphere, 100 g ethyl β-oxo-3-pyridine propionate in 130 g triethyl orthoformate and 400 mL xylene is dissolved. The mixture is refluxed and stirred for about 6 hours, distillating the tops. Once completed the conversion, the mixture is cooled to room temperature and the excess triethyl orthoformate is distilled off under reduced pressure. The residue is taken again with 50 mL xylene, and the mixture concentrated to residue under reduced pressure, yielding 129 g of product as an oil with 85% HPLC titre (A %).

Example 11

6-hydroxy-N-(2-methyl-5-nitrophenyl)-4-(3-pyridyl)-2-pyrimidine amine 4

40 g (2-methyl-5-nitrophenyl)guanidine in 160 mL N-methyl pyrrolidone is dissolved. The mixture is heated to 150° C. and ethyl β-oxo-3-pyridine propionate is added portionwise, to 50 g total in a time period of 5 hours, distillating about 15 g of by-products under a nitrogen flow. At the end of the reaction, the mixture is cooled and diluted with ethanol. The precipitate is filtrated, yielding, upon drying, 46.4 g of product with HPLC purity of 99% (A %), identified through LC-MS and ¹H-NMR.

LC-MS: [M+1]⁺=324.

¹H-NMR (300 MHz, DMSO-d₆): δ (ppm)=2.37 (s, 3H); 6.59 (s, 1H); 7.47 (m, 2H); 7.85 (dd, 1H); 8.36 (dt, 1H); 8.40 (s, 1H); 8.63 (dd, 1H); 9.20 (d, 1H); 9.30 (s, 1H).

Example 12

6-chloro-N-(2-methyl-5-nitrophenyl)-4-(3-pyridyl)-2-pyrimidine amine 7

Under inert atmosphere, 27 g 6-hydroxy-N-(2-methyl-5-nitrophenyl)-4-(3-pyridyl)-2-pyrimidine amine in 125 mL phosphorous oxychloride is suspended, and 11.5 g potassium carbonate is added portionwise. The mixture is heated to 50° C. for 6 hours under stirring. At the end of the reaction, the suspension is concentrated to residue, it is diluted with water, cooled, and the precipitate is filtrated. Upon drying, 26.6 g of product with HPLC purity of 80% (A %) is achieved, identified through LC-MS and ¹H-NMR. Such raw product also contains a by-product, in an amount of about 15% (A %) which, during the following reduction reaction, still yields the desired product (4-methyl-N3-[4-(3-pyridinyl)-2-pyrimidinyl]-1,3-benzenediamine). The raw material, therefore, is employed as is in the example 13.

LC-MS: [M+1]⁺=342; [M+2+1]⁺=344.

¹H-NMR (300 MHz, DMSO-d₆): δ (ppm) 2.37 (s, 3H); 7.49 (d, 1H); 7.83 (m, 2H); 7.92 (dd, 1H); 8.6 (s, 1H); 8.75 (d, 1H); 8.84 (s, 1H); 9.36 (s, 1H); 9.80 (s, 1H).

Example 13

4-methyl-N3-[4-(3-pyridinyl)-2-pyrimidinyl]-1,3-benzenediamine 8

In an autoclave, 5 g 6-chloro-N-(2-methyl-5-nitrophenyl)-4-(3-pyridyl)-2-pyrimidine amine, 0.5 g palladium on charcoal 5% wet with 50% water, 50 mL ethanol and 5 mL triethylamine is charged. The mixture is hydrogenated at 5 bars and room temperature for 40 hours. Once completed the conversion, the catalyst is filtered off and the filtrates is concentrated in vacuum. The residue is taken again with isopropyl acetate and an aqueous carbonate solution. The layers are separated, and the organic layer is concentrated, yielding, upon drying, 3 g of product with 85% HPLC purity (A %), which is identified through LC-MS and ¹H-NMR.

LC-MS: [M+1]⁺=278.

¹H-NMR (300 MHz, DMSO-d₆): δ (ppm) 2.02 (s, 3H); 4.85 (s, 2H); 6.31 (d, 1H); 6.76 (s, 1H); 6.84 (d, 1H); 7.33 (d, 1H); 7.50 (m, 1H); 8.38 (d, 1H); 8.43 (d, 1H); 8.66 (bs, 1H); 9.22 (s, 1H).

The invention claimed is:

1. A process for the preparation of one or more compounds of Formula 1

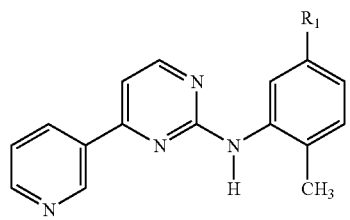

or salts thereof, in which R₁ represents amino, nitro, halogen, hydroxy, NHC(O)R₃, NHR₄, R₃ represents 4-(halo-methyl)phenyl, 4-(hydroxymethyl)phenyl, 4-((4-methylpiperazinyl)carbonyl)phenyl, 4-(alkoxycarbonyl)phenyl, or 4-[(4-methyl-1-piperazinyl)methyl]phenyl, wherein alkoxy means C₁-C₄ alkoxy, R₄ represents a protecting group for the amine group, comprising the steps of:

a) reacting the β-oxo-3-pyridinepropanal, a salt thereof, or compound of Formula 17

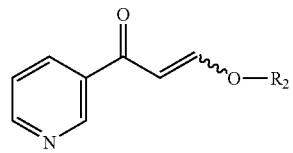

wherein R₂ represents hydrogen, C₁-C₄ alkyl, benzyl, or phenyl,
with an aryl guanidine of Formula 3

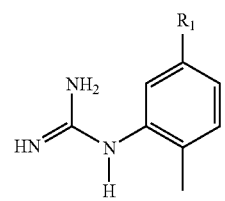

wherein R₁ has the meaning described above, to yield the compound of Formula 19

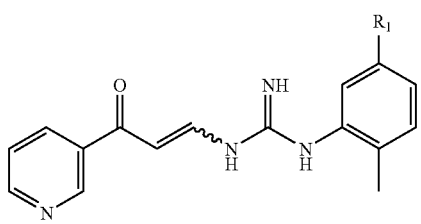

in which R₁ has the foregoing meaning, and b) cyclizing the intermediate of Formula 19 in the presence of a base.

2. The process according to claim 1, wherein R₁ represents amino, nitro, NHC(O)R₃.

3. The process according to claim 1, wherein R₂ represents hydrogen, isopropyl, or n-butyl.

4. The process according to claim 1, wherein R₃ represents 4-(chloromethyl)phenyl, or 4-[(4-methyl-1-piperazinyl)methyl]phenyl.

5. The process according to claim 1, wherein R₄ represents a carboxamide, a sulphonamide, or a carbamate.

6. The process according to claim 1, wherein the base employed in the step b) is selected from the group consisting of sodium hydroxide, sodium carbonate, sodium C₁-C₄ alcoholates, potassium hydroxide, potassium carbonate, potassium C₁-C₄ alcoholates, lithium hydroxide, lithium carbonate, lithium C₁-C₄ alcoholates, caesium hydroxide, caesium carbonate, ammonia, and 4-dimethylaminopyridine.

7. The process according to claim 1, wherein said base is present also in the step a).

8. The process according to claim 1, wherein said base is absent in the step a), and comprising the isolating step of the intermediate of formula 19.

9. The process according to claim 1, wherein the synthesis is carried out in a solvent selected from the group consisting of methanol, ethanol, isopropanol, n-butanol, dimethyl sulfoxide, dimethylformamide, dimethylacetamide, N-methylpyrrolidone, toluene, and mixtures thereof.

10. The process for the preparation of 4-methyl-N3-[4-(3-pyridinyl)-2-pyrimidinyl]-1,3-benzenediamine of Formula 8

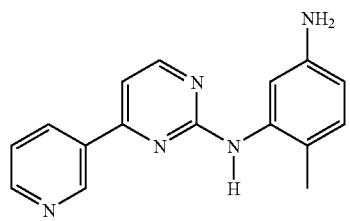

comprising the steps of:

a) reacting the sodium salt of the β-oxo-3-pyridinepropanal of Formula 20 (or a tautomer thereof)

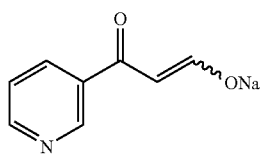

with the (2-methyl-5-aminophenyl)guanidine of Formula 21

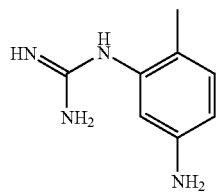

to yield the compound of Formula 22

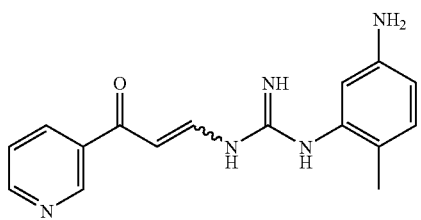

and b) cyclizing the intermediate of Formula 22 in the presence of a base.

11. Process for the synthesis of Imatinib or Imatinib mesylate comprising the steps according to claim 1.

* * * * *